United States Patent [19]

Ellison et al.

[11] Patent Number: Plant 6,968

[45] Date of Patent: Aug. 1, 1989

[54] ASPARAGUS PLANT—'KATHRYN'

[75] Inventors: J. Howard Ellison, Milltown; John J. Kinelski, Princeton, both of N.J.

[73] Assignee: Rutgers University, New Brunswick, N.J.

[21] Appl. No.: 159,683

[22] Filed: Feb. 24, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

An Asparagus plant of unknown parentage selected from an old field of the unpatented variety "Mary Washington" notable for its female characteristics, vigor, and resistance to rust (*Puccinia asparagi*).

1 Drawing Sheet

This invention relates to Asparagus plants and is one of a large number which have either been discovered or produced during a wide-ranging program of Asparagus plant breeding.

Further, during the program referred to, virtually all of the desirable characteristics as well as those not desired, have been encountered.

Among desired characteristics which have been sought during our detailed crossing and re-crossing, is increased rust resistance (*Puccinia asparagi*), which is one of the important contributions of the plant hereof.

Since vigor is also valuable in the commercial aspect of asparagus production, the fact that our new variety also embodies that element is extremely important.

Emphasizing that our new Asparagus plant is a female plant is the fact that we have chosen to designate it by the female name "Kathryn" for commercial identification though that is not the primary emphasis hereof.

The use of our new plant for breeding is a part of the important improvement hereof, it being noted that when combined sexually with the variety "Scott Howard", which is the subject of U.S. Plant Pat. No. 5,549, and F 1 all male asparagus hybrid which we have designated "Jersey Gem" was produced.

"Jersey Gem" is the subject of separate application and has established the value of our program and the instant new plant "Kathryn" set forth herein provided thereby.

We have asexually propagated this new plant by crown division and tissue culture, and found that the vigor and rust resistance referred to are in fact provided in successive generations, establishing that these aspects do come true.

It is of interest that the new plant hereof was selected from an old field of the variety "Mary Washington" (unpatented) in New Jersey, because of the characteristics herein referred to as outstanding.

Figure 2:
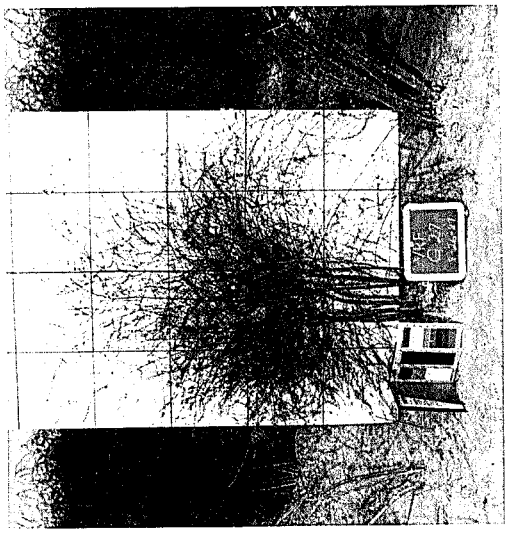
Figure 1:
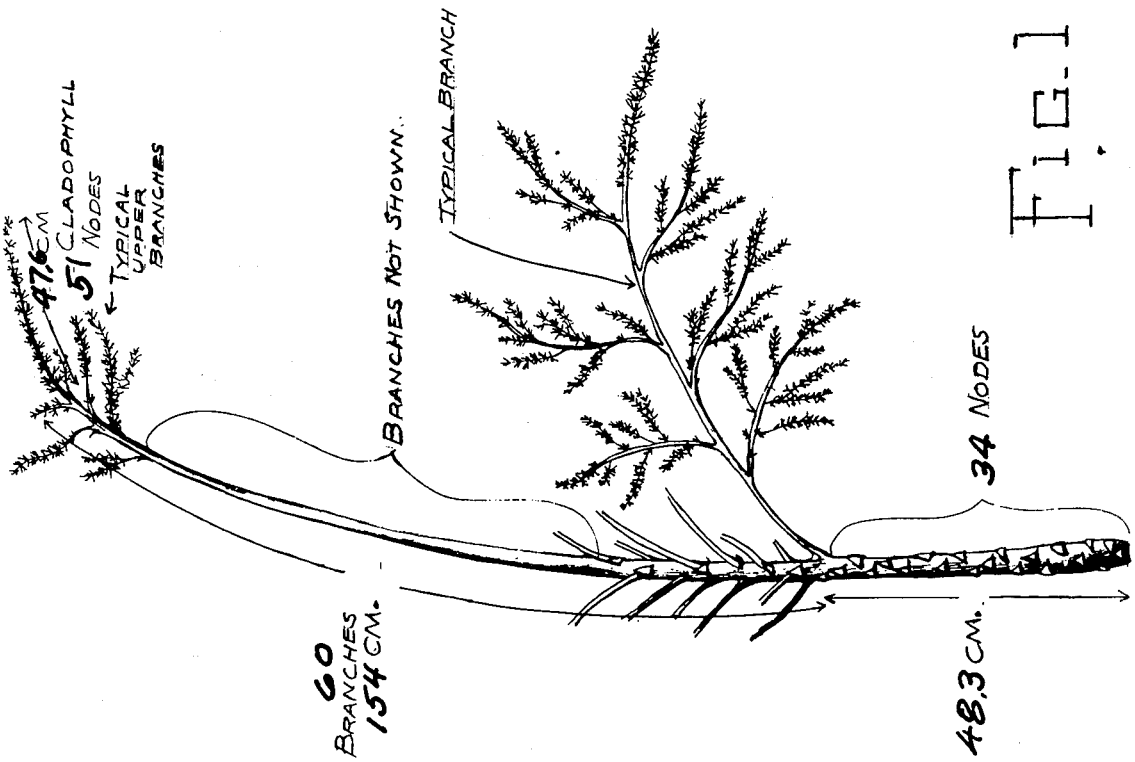

In order to distinguish and identify our new asparagus plant, we have shown in the accompanying drawing a typical plant, wherein FIG. 1 discloses a number of characteristics which appear in the average plant and FIG. 2 shows in color a reproduction representative of such typical plant, with color designations referring to Munsell Limit Color Cascade published by Macbeth Division of Kollmorgen Corporation, and as nearly true as such a color disclosure can be made.

Further details of the plant data are set out in the table below to assist in identifying our new asparagus plant and distinguishing the same from others in our extensive program, such data being derived from a typical plant of "Kathryn".

| ASPARAGUS PLANT DATA | |
|---|---|
| ASPARAGUS PLANT NO. "KATHRYN"(G27 Female) | Inch × 2.54 = cm. |
| STALK DATA | |
| The demensions presented below are expressed in centimeters unless otherwise indicated. The number "1" in parenthesis below, indicates that the measurements presented were taken from the largest stalk. | |
| Number of nodes below first branch(1) | 34 |
| Number of cm. from crown to first branch(1) | 48.3 |
| Number of branches(1) | 60 |
| Number cm. between first and last branch(1) | 154 |
| Internode length in cm. between branches | 2.57 |
| Number of cladophyll nodes beyond last branch(1) | 51 |
| Number of cm. beyond last branch(1) | 47.6 |
| Internode length in cm. beyond last branch(1) | 0.93 |
| Largest stalk diameter in mm | 23 |
| Mean diameter of three largest stalks in mm | 19.8 |
| Number of stalks | 11 |
| Stalk vigor index (Number × mean diameter) | 4312 |
| Mature stalk color, bloom removed | 21.5–13 |
| Crown to first branch of highest headed stalk cm | 48.3 |
| Length of highest headed stalk cm | 250 |
| FLOWER DATA | |
| Petal tip (yellow) | 26–4 |
| Petal base (green) | 21–10 |
| Flower length mm | 4.17 |
| Flower width at midpoint mm | 2.29 |
| FRUIT DATA Kathryn (G27 × 22–8) | |
| Weight of 100 fruit (g) | 23.4 |
| Water displacement of 100 fruit (ml) | 28.0 |
| Number of seed per 100 fruit | 207 |
| Weight of seed per 100 fruit (g) | 6.7 |
| Mean weight per seed (g) | 0.0324 |
| Water displacement of seed of 100 fruit (ml) | 7.5 |
| Mature fruit color | 33–12 |
| CLADOPHYLL DATA | |
| Number per node | 4.87 |
| Length (mm) | 10.50 |
| Width (mm) | 0.123 |

We claim:

1. A new and distinct variety of Asparagus plant as hereinfore shown and described, characterized particularly as to novelty by its female characteristics together with its vigor, resistance to rust (*Puccinia asparagi*) when planted in isolation with a male plant producing F 1 seed.

* * * * *